(12) United States Patent
Hashiba et al.

(10) Patent No.: US 10,154,776 B2
(45) Date of Patent: Dec. 18, 2018

(54) SURGICAL ENDOSCOPE AND PROCESS FOR EXCHANGING SURGICAL TOOLS IN A SURGICAL ENDOSCOPE

(75) Inventors: Kiyoshi Hashiba, São Paulo (BR); Dorival Zito Filho, São Paulo (BR); Pablo Rodrigo de Siqueira, São Paulo (BR); Hélio Shigueki Ozawa, São Paulo (BR)

(73) Assignee: SOCIEDADE BENEFICENTE DE SENHORAS HOSPITAL SIRIO LIBANES, Sao Paulo-SP (BR)

( * ) Notice: Subject to any disclaimer, the term of this patent is extended or adjusted under 35 U.S.C. 154(b) by 962 days.

(21) Appl. No.: 12/899,116

(22) Filed: Oct. 6, 2010

(65) Prior Publication Data

US 2011/0077460 A1    Mar. 31, 2011

Related U.S. Application Data

(63) Continuation-in-part of application No. PCT/BR2009/000203, filed on Jul. 13, 2009.

(30) Foreign Application Priority Data

Jul. 11, 2008   (BR) ...................... 0802525

(51) Int. Cl.
*A61B 1/00* (2006.01)
*A61B 1/04* (2006.01)
*A61B 1/018* (2006.01)

(52) U.S. Cl.
CPC .......... *A61B 1/018* (2013.01); *A61B 1/00098* (2013.01)

(58) Field of Classification Search
CPC .............. A61B 1/00073; A61B 1/0008; A61B 1/00098; A61B 1/00133; A61B 1/00149
(Continued)

(56) References Cited

U.S. PATENT DOCUMENTS 3,915,157 A   10/1975 Mitsui
5,460,168 A   10/1995 Masubuchi et al.
(Continued)

FOREIGN PATENT DOCUMENTS

EP         1 985 226 A    10/2008
WO    WO 2008/070556 A    6/2008

OTHER PUBLICATIONS

International Search Report and Written Opinion for International Appl. No. PCT/BR2009/000203 dated Oct. 8, 2009.

*Primary Examiner* — Alexandra L Newton
*Assistant Examiner* — Rynae Boler
(74) *Attorney, Agent, or Firm* — Alston & Bird LLP

(57) ABSTRACT

It is described an endoscope to perform surgeries preferably by perforation in translumenal organs in internal organs, comprising an insertion tube (10') having a distal end (12') and at least two working channels, one working channel having a smaller diameter (20') and one working channel having a larger diameter (30'), the working channels (20', 30') being capable of receiving surgical tools, the endoscope comprising at least two command cables (9') operatively associated with the working channel of smaller diameter (20') and at least two command cables (9') operatively associated with the working channel of larger diameter (30'), the command cables (9') being capable of allowing the surgical tool, arranged on any of the working channels (20',30'), to move in any direction, regardless of the movement of the distal end (12') of the insertion tube (10').

The endoscope is capable of performing endoscopic surgeries in places of difficult access, through the use of surgical tools which can contour organs or tissues, keeping the position of the distal end (12') of the insertion tube (10'), (Continued)

being also capable of replacing the surgical tool without the need of exchanging the entire distal end (12'), apart from facilitating disinfection.

11 Claims, 6 Drawing Sheets

(58) Field of Classification Search
USPC ....... 600/104, 106, 153, 107, 127, 129, 149, 600/152, 154–158, 172–175
See application file for complete search history.

(56) References Cited

U.S. PATENT DOCUMENTS

| | | | |
|---|---|---|---|
| 5,797,835 A | 8/1998 | Green | |
| 6,059,719 A | 5/2000 | Yamamoto et al. | |
| 6,352,503 B1 | 3/2002 | Matsui et al. | |
| 6,458,074 B1 | 10/2002 | Matsui et al. | |
| 6,569,085 B2 | 5/2003 | Kortenbach et al. | |
| 7,537,561 B2 * | 5/2009 | Yamaya et al. | 600/106 |
| 8,092,371 B2 * | 1/2012 | Miyamoto et al. | 600/106 |
| 2003/0040657 A1 * | 2/2003 | Yamaya | A61B 1/00039 600/107 |
| 2005/0234294 A1 * | 10/2005 | Saadat | A61B 1/0008 600/104 |
| 2005/0272975 A1 * | 12/2005 | McWeeney et al. | 600/113 |
| 2008/0039690 A1 | 2/2008 | Zubiate et al. | |
| 2008/0051631 A1 * | 2/2008 | Dejima et al. | 600/114 |

\* cited by examiner

*PRIOR ART*

SURGICAL ENDOSCOPE AND PROCESS FOR EXCHANGING SURGICAL TOOLS IN A SURGICAL ENDOSCOPE

CROSS REFERENCE TO RELATED APPLICATIONS

The present application is a continuation-in-part of PCT/BR2009/000203 having an international filing date of Jul. 13, 2009, which claims priority to BR PI0802525-8 filed on Jul. 11, 2008, each of which is incorporated by reference herein in its entirety.

FIELD OF THE INVENTION

The present invention refers to a surgical endoscope to be preferably used in surgeries held through translumenal natural orifices (NOTES), which can also be used in laparoscopic and endoscopic surgeries or in any other operative procedure where its use is feasible.

BACKGROUND

An endoscope is a device which basically comprises an insertion tube, being normally inserted inside the gastrointestinal, respiratory and urinary tract, among others, allowing doctors to verify in loco possible endolumenal alterations.

Apart from being extremely effective to enable endolumenal examination and the diagnosis of diseases, endoscopes have been increasingly used for endoscopic surgeries. The many endoscopic surgeries that may be held include the treatment of certain esophageal diverticula, certain benign tumors and the initial tumors in the esophagus, stomach, duodenum and large intestine, gastric and esophageal varices, bleeding ulcers, removal of bile duct calculi and treatment of chronic pancreatitis, among others.

Due to the absence of incisions in the skin and openings, the technique known as NOTES (Natural Orifice Translumenal Endoscopic Surgery) may be used in endoscopic surgeries (endosurgeries), once it enables, among other advantages, a faster and less painful postoperative recovery, apart from the lack of infections once there are no incisions. However, to make the technique called NOTES possible, the endoscope must have a set of constructive and operational features which enable it as an operation platform for surgical tools.

U.S. Pat. No. 5,797,835 describes a surgical device for use in endoscopy and endosurgery comprising a set formed by two endoscopic devices externally interconnected and inserted in a given part of the body of the patient to be operated in two different points of entry. However, this kind of device is used for application through external incisions in the patient's body, leaving scars and requiring the application of stronger anesthesia, raising the risks of the procedure.

U.S. Pat. No. 6,569,085 discloses a method and a device to provide an endosurgical tool arranged on the exterior of an endoscope for positioning through an unnatural open orifice, implemented by incision, in the body of a patient. This equipment allows tools to be inserted and positioned over the exterior of the endoscope, when this is positioned within the patient's body. Particularly, the patent seeks to solve the problem of how to insert the tools when they have a very large diameter for insertion through the working channel of the endoscope.

However, this type of endoscope has intrinsic limitations, once it facilitates, or at least it does not reduce, the chances of injuries in the patient's organs and the occurrence of infections.

U.S. Pat. No. 6,458,074 discloses a surgical endoscope comprised by two oblong working channels, one of them being vertical and the other one, horizontal. The channels have mechanisms or supports that allow the tools arranged inside them to perform vertical movements, in the vertical oblong working channel, and horizontal movements, in the horizontal oblong working channel. According to the patent, this endoscope makes it possible to reach a broader working area, once the tools move without displacing the tip of the endoscope.

Furthermore, the constitution of the tip of the endoscope limits a lot the size of the medical tools to be manipulated, making it impossible to use the equipment when it is necessary to employ very sharp tools or tweezers with high seizing capacity.

Document WO 2008/070556 describes a conductive tube comprised by an endoscope (fixed platform) and by tubes that conduct its accessories (light guide, objectives, air/water channel), assembled on a platform where several surgeons concomitantly handle the tube and the accessories. It is a very complex device, which works, in fact, as a plurality of physically and operatively associated endoscopes, requiring the presence of several surgeons to operate it, which, in practice, ends up making its use difficult. Furthermore, in comparison with the endoscope of the present invention, this complex device only allows exchanging the tools by removing them through the proximal region of the tube, in other words, the one located outside the patient's body and close to the surgeons who operate him.

In short, it is possible to state that the state of the art related to endoscopic devices used in internal surgeries comprises only combined devices for endoscopic/laparoscopic use, devices which have only two working channels and devices installed externally to the body of an endoscope.

Furthermore, the endoscopes of the state of the art do not allow exchanging the surgical tools through the distal part.

Thus, for the performance of surgeries through translumenal orifices it was develop a unique endoscope which allowed the tools arranged on the working channels to move independently, and which also allowed exchanging the surgical tools through the distal end of the endoscope, expanding the range and the dimensions of the tools to be used.

Embodiments of the present invention aim at providing a surgical endoscope for the performance of surgeries through translumenal orifices (NOTES), which allows carrying out surgeries by means of a single device, without the need of making additional orifices in the patient's body.

Embodiments of the present invention also aim at providing a surgical endoscope for the performance of surgeries through translumenal orifices (NOTES), which allows each surgical tool arranged on each one of the working channels to move freely and independently, expanding their operative capacity.

Embodiments of the present invention further aim at providing a surgical endoscope which allows exchanging surgical tools easily and with a great interchangeability capacity.

Another exemplary purpose of the present invention is to provide a quick, simple and safe process for replacing the surgical tools of the endoscopes, from its distal end.

BRIEF SUMMARY OF THE INVENTION

The goals of this invention, according to one embodiment, are achieved by an endoscope to perform surgical operations preferably through the translumenal orifices in internal organs, comprising an insertion tube with a distal end and at least two working channels, one working channel having a smaller diameter and one working channel having a larger diameter, the working channels enabling the operation of at least a surgical tool, the endoscope comprising at least two command means operatively associated with the working channel of smaller diameter and at least two command means operatively associated with the working channel of larger diameter, the command means being capable of allowing the surgical tool to freely move in relation to axes x, y and z, regardless of the movement of the distal end of the insertion tube.

The goals of the present invention according to one embodiment are also achieved by an endoscope to perform surgical operations preferably through translumenal orifices in internal organs, comprising an insertion tube with a distal end and at least two working channels, one working channel having a smaller diameter and one working channel having a larger diameter, the working channels being capable of receiving at least a surgical tool, the endoscope comprising a vertical basis guide and a horizontal basis guide, the vertical basis guide being operatively arranged on the working channel of smaller diameter of the distal end, in a first cavity, and the horizontal basis guide being operatively arranged on the working channel of larger diameter of the distal end, in a second cavity.

The goals of the present invention according to one embodiment are also achieved by a process for exchanging surgical tools in surgical endoscopes, comprising the following steps:
  i) Removal of the insertion tube from an orifice in the body of a patient;
  ii) Removal of at least a surgical tool associated with the distal end of the insertion tube;
  iii) Placement of at least a surgical tool associated with the distal end of the insertion tube; and
  iv) Introduction of the insertion tube in the orifice.

The advantages of the present invention include using a single equipment (endoscope) for the performance of an endoscopic surgery which allows the replacement the surgical tools directly at the distal end, without the need of passing them through the internal working channels, which restricted the type and size of the tool that can be replaced.

BRIEF DESCRIPTION OF THE DRAWINGS

The present invention will be further described in more details based on an example of implementation represented in the drawings. The figures show.

DETAILED DESCRIPTION OF THE DRAWINGS

As known by the ones skilled in the art and corroborated by the analysis of U.S. Pat. No. 6,458,074, the surgical endoscopes currently known comprise two working channels, enabling their use in abdominal and thoracic surgeries through perforations in digestive organs.

Figure 1:
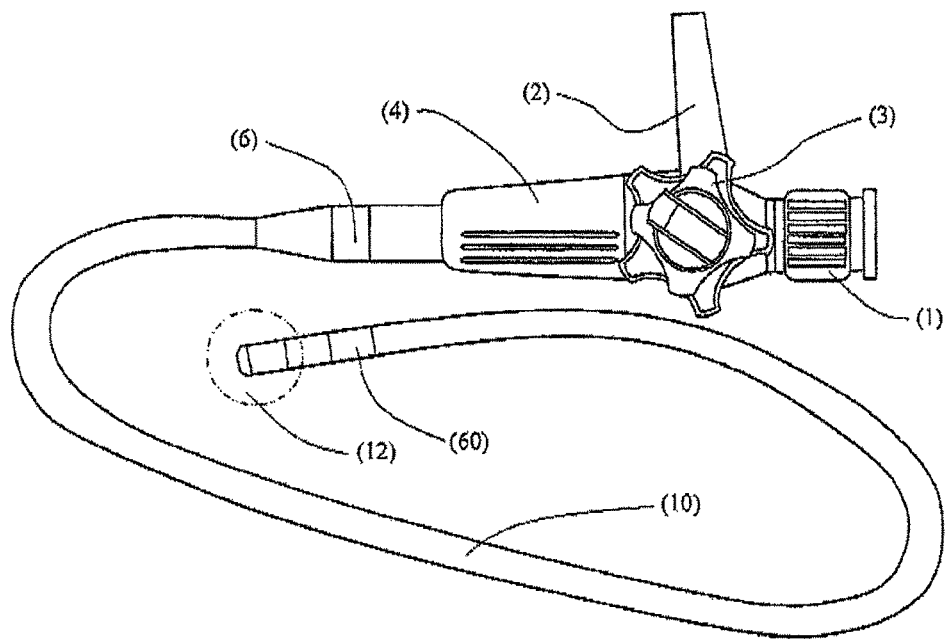
FIG. 1—a view in general perspective of any endoscope belonging to the state of the art.
Figure 2:
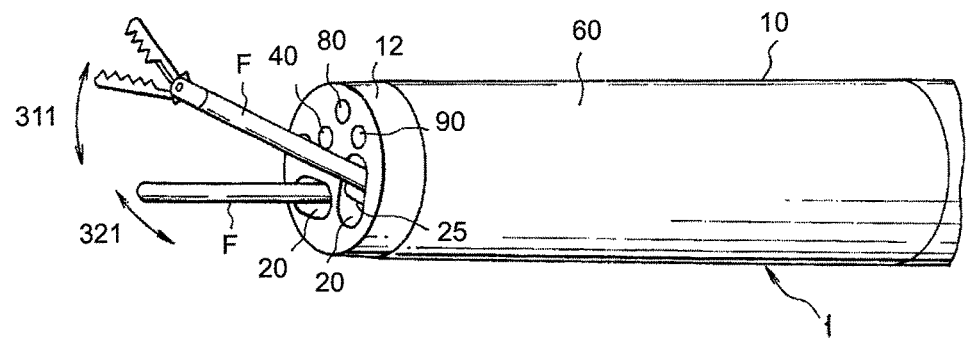
FIG. 2—a detailed view of the distal end (which is inserted in the patient's body) of any surgical endoscope belonging to the state of the art.
Figure 3:
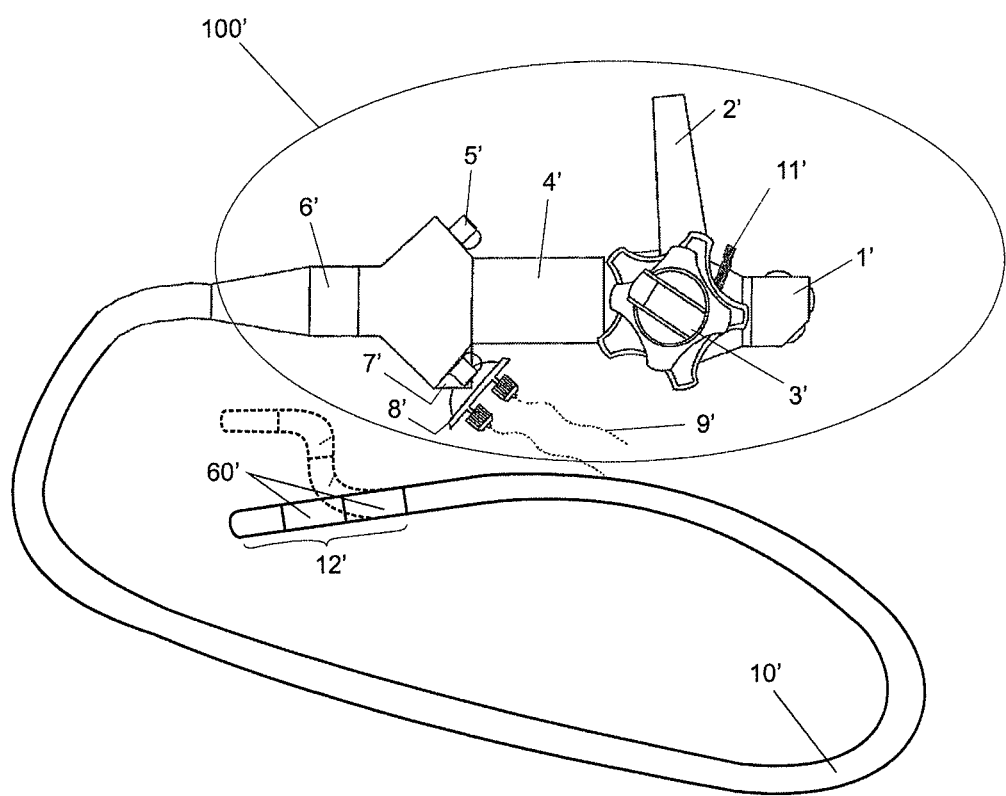
FIG. 3—a view in general perspective of the surgical endoscope covered by one embodiment of the present invention.

FIGS. 1 and 2 attached disclose an endoscope of the state of the art which basically comprises a body 4 with which the following are associated: an eyepiece 1, a light guide 2, angling commands 3 and, on the other side, an insertion tube 10 which is elongated and substantially cylindrical. The body 4 offers support to the eyepiece 1, to the light guide 2, to the angling commands 3 and is arranged on the proximal end of the endoscope.

The end of the endoscope turned to the surgeons who will handle it, which is exactly the body 4, is called proximal end, whereas the opposite end of the endoscope, positioned at the tip of the insertion tube 10, is the distal end 12.

Thus, the insertion tube comprises the distal end 12, which is free, and another end 6, which is rigidly associated with the body 4. Adjacent to the distal end 12, there is a flexible section 60.

The eyepiece 1 enables the visualization through the distal end 12, allowing the surgeon to observe inside the patient's body, whereas the light guide 2 enables exactly the illumination of the body in the region where the distal end is positioned. The angling commands 3, on their turn, are operatively associated with the distal end 12, preferably by means of steel cables, allowing the surgeon to move it remotely. Due to the existence of the flexible section 60, the distal end 12 can move in relation to the rest of the insertion tube 10.

Preferably, the endoscope has a plurality of longitudinal passages. Some passages serve to enable the movement of the distal end of the endoscope, which will be described later, and other passages serve to enable the operation of the lens and illumination systems.

To make the illumination system possible, for instance, it is provided a passage of light 90 which makes the link between the light guide 2 and the distal end 12. Preferably, this passage comprises a fiber optical beam, a material which has the property of conducting light without the event of considerable dispersion. This way, a light source such as an incandescent lamp or the like is positioned in the light guide 2 and the light beams emitted by it are conducted by the fiber optical beam up to the distal end 12, when then they leave the endoscope and illuminate inside the patient's body. Alternatively, with the technological evolution experienced by LEDs, it became possible to position one or more LEDs directly in the distal end 12 and to use the respective passage to enable the supply of electric current.

However, the lens system also requires a passage comprising another fiber optical beam, which makes the link between an objective lens 40 present in the distal end 12 and the eyepiece 1. Thus, the rays of light regarding the image of the inner side of the patient's body (possible to be viewed thanks to the existence of the illumination system previously mentioned) reach the lens 40 present in the distal end 12, pass along the fiber optical beam and reach the eyepiece 1. In the most modern endoscopes, this system has been replaced with a camera located in the distal end, a situation in which the corresponding passage becomes superfluous, and the space occupied by it can be used for the passage of electric connections which (i) electrically feed the camera and (ii) enable the transmission of the captured images. If a camera exists, the eyepiece is replaced with a small monitor located in the body of the endoscope or, which is preferable, the endoscope is connected to external monitors that allow an extremely superior visualization.

Also alternatively, it is possible to use a camera which runs on battery and has means for performing the transmission of the images by radiofrequency, a situation in which the respective passage is no longer necessary, leaving room for the expansion of the diameter of the channels aimed at handling the operative tools, for instance.

FIG. 2 illustrates, in highlight, the distal end 12 of the insertion tube 10 of an endoscope that belongs to the state of the art. In this figure, there is a detailed visualization of the main channels and passages of this equipment.

Besides the components previously mentioned, FIG. 2 enables the visualization of two working channels 20 (which allow the passage and handling of surgical tools F such as tweezers, scissors and scalpels, etc.) and, additionally, of a insufflation channel 80, which enables to insufflate air, water or any other liquid inside the patient's body should this procedure be necessary.

Evidently, the working channels 20 extend from the distal end 12 up to the body 4, allowing the surgeon to control the movements of the surgical tools F. In this regard, bases 25 are supplied, arranged inside the channels 20, adjacently to the distal end 12, which support the tools F and allow them to move. As it is possible to see in FIG. 12, one of the surgical tools F can be moved in the vertical direction 321 and the other, in the horizontal direction 320.

For said purpose, each one of the bases 25 is connected to one or two steel cables (not illustrated) which, manipulated by the surgeon, allow said movement 320,321. For the correct positioning and sliding of these steel cables, respective dedicated passing channels (not illustrated either) are provided, which are parallel and adjacent to the working channels 20.

Furthermore, in order to make the movement of the tools possible, the working channels preferably have oblong shape in the distal end 12, as it can be seen in FIG. 2.

Then, the surgeon manipulates the controls of the cables from the bases 25 (which define the respective longitudinal passages that allow them to extend up to the distal end 12 through the body 4) to position each tool F at the accurate position and then manipulates the control of the tools themselves (whose driving cables pass directly through the working channels 20).

Moreover, before each tool F is positioned, the surgeon manipulates the angling commands which, also by means of steel cables positioned inside longitudinal passages, perform the movement/flexion of the flexible section 60.

The endoscope disclosed in FIGS. 1 and 2 allows the tools F to be correctly and easily positioned for the surgical procedure, although it has some insuperable disadvantages in view of its architecture, namely:

(i) there is not much amplitude of movements to put a tissue away from the body aiming at a better scenario for the performance of the surgical procedure;

(ii) the surgical tools are exchanged and positioned, when possible, by means of the working channels 20, that is, they are removed and positioned through the channels without having the endoscope removed from inside the patient's body. As the full diameter of the endoscope is limited, to have it (endoscope) inserted in the orifices of the patient's body, there is obviously a limitation in the diameters of the working channels 20 and, as a consequence, the range of surgical tools that can be used are just as limited. Particularly, this type of endoscope cannot be used as a platform for the use of tweezers and scalpels of high power/capacity or suture tools. In short, interchangeability is largely limited.

The endoscope covered by the present invention, on the one side, presents some characteristics that are common in the endoscopes currently known, but, on the other side, is innovative, once it presents high interchangeability of surgical tools, more accuracy in the positioning thereof and higher capacity of having the tools deviate from some tissue and/or act in another direction rather than directly towards the working channels 20.

Conceptually, the endoscope covered by the present invention presents countless differences when compared to the endoscopes that belong to the state of the art, although some of their components are similar.

Thus, analogously, an embodiment of the endoscope covered by the present invention also has a body 4' to which the following items are associated: on one side, an eyepiece 1' or the like, a light guide 2' or the like, angling commands 3' and, on the other side, an insertion tube 10' elongated and substantially cylindrical.

Also analogously, the body 4' of the endoscope covered by the present invention, which is turned to the surgeons who will handle it, is called proximal end, whereas the opposite end of the endoscope, positioned on the tip of the insertion tube 10', is called distal end 12'.

The insertion tube 10' comprises the distal end 12', which is free, and another end 6', which is rigidly associated with the body 4'. Adjacently to the distal end 12', a flexible section 60' is provided, preferably comprised by two segments, or sets, of vertebrae which enable movements towards any direction according to axes x, y and z in the space, which will be mentioned further on.

Just as mentioned for the endoscope from the state of the art illustrated in FIGS. 1 and 2, the endoscope covered by one embodiment of the present invention also has, at least, a passage of light 90' (in fact, it preferably has two) which makes the link between the light guide 2' (where the luminous source is positioned) and the distal end 12. For said purpose, each passage of light 90' comprises a respective optical fiber beam and the rays of light generated by the luminous force positioned at the light guide 2' are conducted by the optical fiber beams up to the distal end 12', when they then leave the endoscope and start illuminating inside the patient's body.

Advantageously and preferably, there is/are one or more LEDs directly positioned on the distal end 12', when then the respective passages 90' may present a quite reduced diameter (only to enable the housing of the electric connections for current supply). With that, there is more space left in the transversal section of the insertion tube 10' for the raise in the number of working channels (or expansion of their diameters), which are really essential to the equipment, that is, those which allow the surgical tools to be operated and moved.

There is also a passage that houses another fiber optical beam, which makes the link between an objective lens 40' present in the distal end 12 and the eyepiece 1, wherein, preferably, this passage is positioned in a very centralized or concentric manner, in the body 4, having as basis the cylindrical transversal section of the insertion tube 10'.

Due to the existence of the objective lens 40', the rays of light regarding the image of the inner side of the patient's body (possible to be viewed thanks to the existence of the illumination system previously mentioned) reach the lens 40' present in the distal end 12', pass along the fiber optical beam and reach the eyepiece 1'. However, in a quite preferable manner, this system is replaced with a camera located in the distal end 12' (not illustrated in the figures), which generates images and sends them through at least a pair of wires positioned in the corresponding passage (which may present a smaller diameter once it merely needs to house the electric connections which (i) electrically feed the camera and (ii) enable the transmission of the captured images).

When the endoscope has the camera, preferably, the images are transmitted to one or more external monitors that provide surgeons with an exceptional visibility for work, making the eyepiece 1' absolutely unfeasible and unnecessary. Alternatively, the images from the camera can be sent to a small monitor directly positioned at the body 4', in the place where the lens 1' would be located.

Also alternatively, the endoscope uses a camera run on battery and which has means for performing the transmission of the images by means of radiofrequency, a situation in which a passage to house electric connections is no longer necessary, leaving room for the expansion of the diameter of the working channels.

The endoscope also has an insufflation channel 80', which enables to insufflate air, water or any other liquid inside the patient's body should this procedure be necessary.

Additionally, the body 4' further comprises one or more angling commands 3', one or more levers 11' and at least a support for rocker arms 7',8'.

The angling commands 3', also present in the endoscopes currently known, allow the movement/flexion/guidance of the flexible section 60' which, when comprised by two segments of vertebrae, can move towards any direction according to axes x, y and z in the space, taking on, for instance, the behavior of a "S" whose free end (distal end 12') can freely rotate and turn towards any direction and side, making it possible to correctly position it with much accuracy.

However, the support for rocker arms comprises a support 7' associated with the body 4' in which it is arranged a rocker arm 8' which drives one or more command means, preferably in the form of cables 9' (and preferably two cables 9'), making it possible the movement of a horizontal platform 50' which will be described further ahead. Preferably, a support for rocker arms 7',8' is supplied to each one of the working channels of the endoscope, which will described in details further ahead. Evidently, the supports for rocker arms can be replaced with any other functional elements, which are necessary or desirable, such as a lever 11, and the cables may also be replaced with any other command means 9', and the resulting invention will still be included in the protection scope defined by the attached claims.

Figure 4:
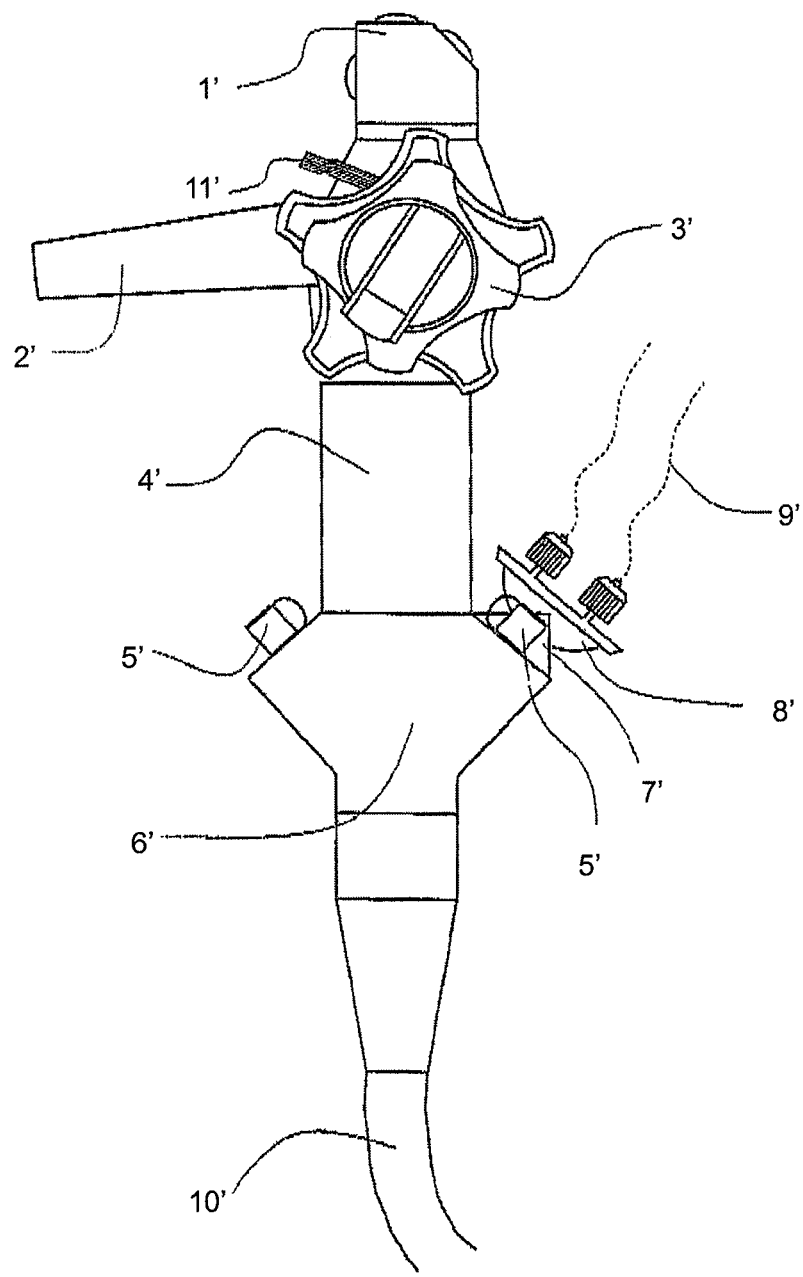
FIG. 4—an upper view of the proximal end of the endoscope covered by the present invention.

Considering a possible configuration of the endoscope covered by an embodiment of the present invention, illustrated in FIG. 4, the angling commands take on the shape of two concentric wheels positioned towards the free end of the body 4', adjacently to the light guide 2' and to the eyepiece 1'.

Positioned in a more meridional position are the support(s) for rocker arms 7',8', which obliquely project themselves in relation to the longitudinal center line of the body 4', at an intermediate section 6' (or operation section) of the body 4'.

The insertion tube 10' of the endoscope covered by embodiments of the present invention comprises at least two working channels 20',30', one working channel having a smaller diameter 20' and the other working channel having a larger diameter 30'. Still preferably, the endoscope also has a third working channel which has a diameter analogous to the smaller channel, 20', and, for this reason, analogously identified. In other words, preferably, the endoscope has one working channel of larger diameter 30' and two working channels of smaller diameter 20'.

The working channels 20',30' enable the operation of said surgical tools F, such as tweezers, scalpels, scissors, tools for suture, etc.

Said command means 9', which, in a preferable but not mandatory manner, take on the form of steel cables, are operatively associated with the working channel of smaller diameter 20' and with the working channel of larger diameter 30', so that there is, at least, two steel cables 9' operatively associated with the channel 20' and at least two steel cables 9' associated with the channel 30'. In fact, it is said that the cables are operatively associated with the channels because they allow the endoscope to work, but they are not positioned inside, or through, the channels. As it can be seen especially in FIG. 5', each steel cable 9' has an own passage which houses it.

The command means, or cables, 9', allow, at a last analysis, the respective surgical tools F respectively associated with the larger and smaller working channels 30',20' to freely move towards all possible directions (in relation to the axes x, y and z), regardless of the movement and position of the distal end 12'. In other words, it is possible that a certain surgical tool F (tweezers, for instance) move in a way that is completely perpendicular, or orthogonal, to the longitudinal length of the insertion tube 10'.

These movements are possible in view of the existence of at least a vertical basis guide 70' and at least a horizontal basis guide 50', where the vertical basis guide 70' is operatively associated with the working channel of smaller diameter 20' and the horizontal basis guide 50' is operatively associated with the working channel of larger diameter 30'.

In a more detailed description, the command cables 9' are, on the one side, physically linked to the supports for rocker arms 7',8' (in the body 4') and, on the other side, physically linked to the vertical basis and horizontal basis guides 70',50', in a way that each pair of cables is linked, on the one side, to a respective rocker arm 8' and, on the other side, to a respective basis guide.

When the surgeon moves a rocker arm 8', (for instance, the rocker arm which will move the vertical basis guide 70'), the movement of this rocker arm will mean that a cable 9' is "pulled" in one direction and the other one is, concomitantly, "pulled" in the same direction and opposite side. As a result the vertical basis guide 70' will move in a certain direction (for instance, upwards, such as it can be seen in FIG. 7). If the rocker arm 8' is moved in the opposite side, each one of the cables is pulled in the opposite side, producing the movement of the vertical basis 70' in the same direction and in opposite side.

Figure 7:
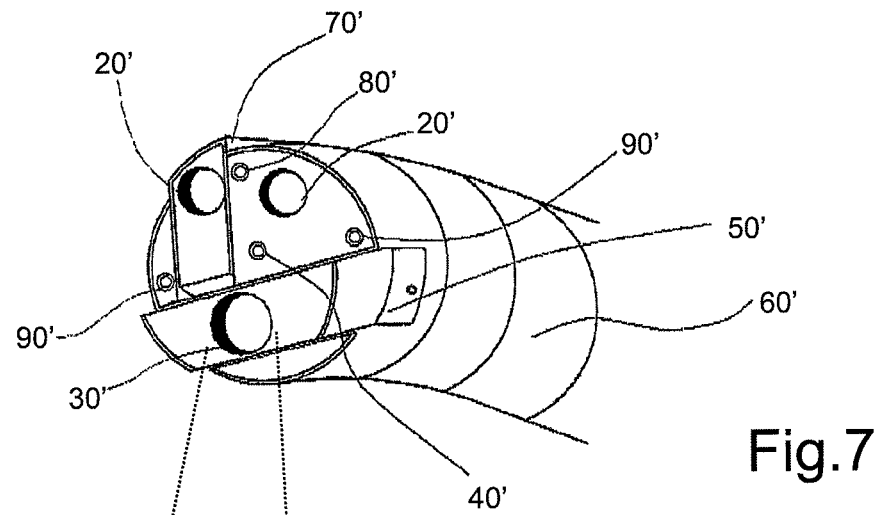
FIG. 7—a third perspective view of the distal end of the endoscope covered by one embodiment of the present invention, where the horizontal and vertical guiding bases are respectively in position of horizontal movement and vertical movement.
Figure 8:
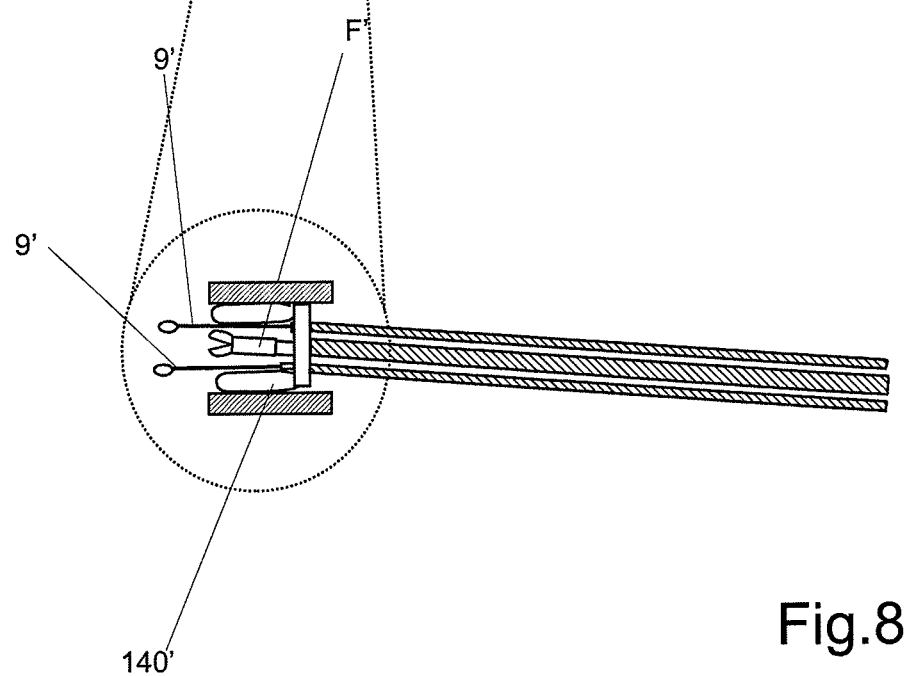
FIG. 8—a sectional view of the distal end of the surgical endoscope covered by one embodiment of the present invention, where the horizontal and vertical guiding bases were removed.
Figure 9:
FIG. 9—a detailed view of the vertebrae comprised on the flexible section 60 of the endoscope covered by one embodiment of the present invention.

The same description applies, mutatis mutandis, to the movement of the horizontal basis 50', except for the fact that the movement will be vertical (see again FIG. 7).

In the preferred embodiment of the invention, the vertical basis guide 70' is moved from a lever 11 (see FIG. 4) which pulls a pair of steel cables 9'. With this, the guide is capable of moving a surgical tool F (which is per se commanded by the working channel of smaller diameter 20'), in a such a way that the tool F can be positioned, or "driven" exactly in the desired place, when the surgeon moves the lever 11.

The horizontal basis guide 50', on its turn, is moved from a rocker arm 8' (see FIG. 4) which pulls another pair of steel cables 9', and, with this, the guide is capable of moving the surgical tool F (which is per se commanded by the working channel of larger diameter 30'), in such a way that the tool F can be positioned, or "driven" exactly in the desired place, when the surgeon moves the rocker arm 8'.

As it can be seen in FIG. 7, both basis guides 70',50' are fastened to the command cables 9' at their back or bottom portion.

It is said that the steel cables 9' and the basis guides 70',50' are operatively associated with the working channels 20',30' because, when the cables move the guides, they allow the surgical tools F which are commanded through the working channels to be correctly positioned and driven, thereby offering to the surgeon more flexibility to operate anywhere, putting tissues away, making incisions, suturing, etc.

As to the third working channel of smaller diameter 20', it preferably does not have any basis guide associated with it, in a way that an occasional tool F installed therein will not be able to be operational at other directions rather than substantially longitudinally in relation to the insertion tube 10'. However, this constructive characteristic is not a coincidence, once the endoscope covered by the present invention was thus configured so that its efficiency and versatility in operations was maximized.

However, nothing prevents a basis guide associated with the third channel from existing; or its construction from being diverse, and also the resulting invention would be included in the scope of protection of the present claims. Finally, nothing prevents the endoscope from having more than three working channels, if necessary or desirable.

Figure 5:
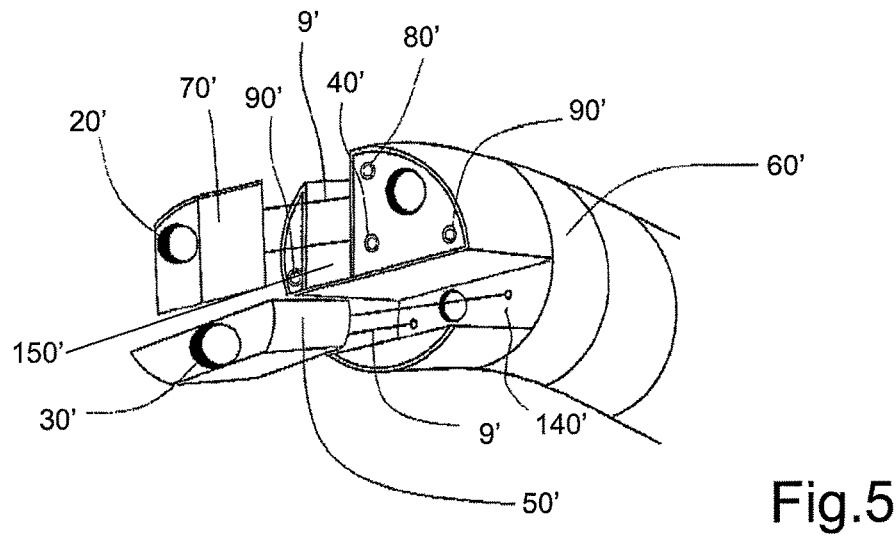
FIG. 5—a first perspective view of the distal end of the surgical endoscope covered by one embodiment of the present invention, being possible to see the vertical and horizontal guiding bases.
Figure 6:
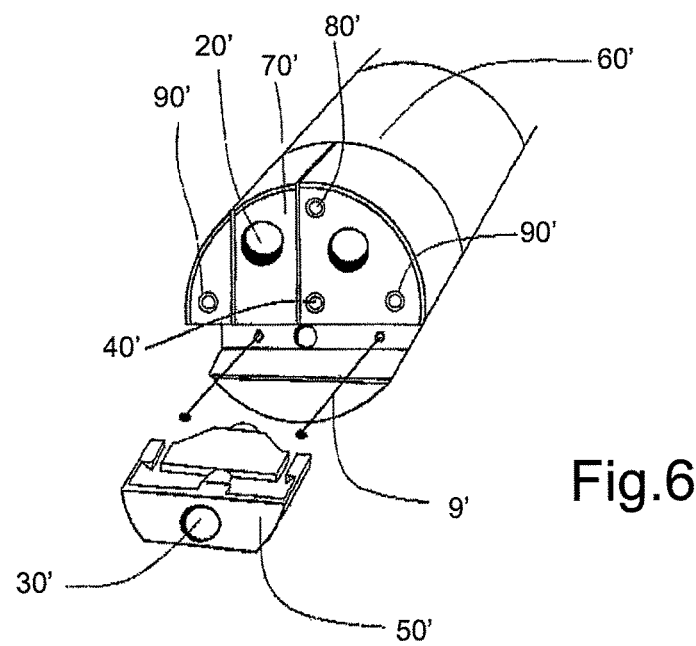
FIG. 6—a second perspective view of the distal end of the endoscope covered by one embodiment of the present invention, in which the horizontal guiding basis was removed.

Another important characteristic of the invention lies in the fact that the basis guides 70',50' are positioned in cavities that exist in the distal end 12', as it can be seen especially in FIGS. 5 and 6. Comparing them with FIG. 2 makes it even clearer the existence of these cavities.

The vertical basis guide 70' is arranged on a first cavity 150', defined in the end of the working channel of smaller diameter 20', whereas the horizontal basis guide 50' is arranged on a second cavity 140', defined in the end of the working channel of larger diameter 30'.

This means that, when the endoscope is inserted in an orifice of the patient's body, the basis guides 70',50' and the surgical tools present therein are not protuberant; but, in fact, in a "retreated" position in relation to the rest of the distal end 12', not resulting in any trauma in the patient's body.

However, this is not a single advantage; on the contrary, this architecture brings about a series of characteristics that make the present endoscope quite more attractive.

In the first place, the considerable space arranged on the cavities 140',150' allows the positioning of surgical tools F which are stronger and have larger dimensions. This translates, for instance, into the possibility of using more powerful tweezers, quicker and more efficient equipment to suture, among other advantages, expanding the scope of use of the endoscope.

Due to the fact that the basis guides 70',50' and the surgical tools included therein are in "retreated" position in relation to the rest of the distal end 12', minimizing the injury caused to the patient, it is possible to remove the endoscope during the surgical procedure, to exchange the necessary surgical tools F and to insert it again.

This possibility of exchanging surgical tools during the operative procedure, combined with the fact that they can be correctly positioned and used as a whole, is a huge operational advantage. For instance, it is possible to use tweezers and scalpels to perform a biopsy, to remove the endoscope from inside the patient's body, to remove the piece of tissue which was in the tweezers, to exchange the tools by other ones that allow suture or cauterization, to insert again the endoscope in the orifice of the patient's body and to treat the injury.

In some endoscopes currently known, it can be possible to exchange the surgical tools F during surgery; however, this is made through the working channels, without removing the endoscope from inside the patient's body, restricting a lot the type and size of the tool that can be replaced.

In the endoscope covered by an embodiment of the present invention, as the surgical tools F are replaced from the distal end 12', outside the patient's body, without being necessary to have them passing through the working channels, there is no such limitation in the size of the tools, with the advantages already disclosed above.

Once it is ease to disassemble the basis guides 70',50' and the surgical tools, the endoscope covered by embodiments of the present invention can be cleaned and sterilized much more quickly and easily than the endoscopes currently used.

Finally, the endoscope covered by an embodiment of the present invention allows a process for exchanging surgical tools F which comprises the following steps:
  i) Removal of the insertion tube 10' from an orifice in the patient's body;
  ii) Removal of at least a surgical tool associated with the distal end 12' of the insertion tube 10';
  iii) Placement of at least another surgical tool associated with the distal end (12') of the insertion tube (10'); and
  iv) Reintroduction of the insertion tube in the orifice.

In this step iii), the surgical tool can be associated both with the first cavity 150' and with the second cavity 140'.

After describing an example of preferred embodiment, it shall be understood that the scope of the present invention encompasses other possible variations, being limited only by the contents of the attached claims, where the possible equivalents are included.

The invention claimed is:

1. Endoscope to perform surgeries through translumenal orifices in internal organs, said endoscope comprising:
  an insertion tube comprising:
    a distal end having an outer periphery, at least one outer surface, and at least one open-ended recessed portion having first and second opposing open ends and first and second opposed recess surfaces spaced apart from one another and each extending continuously between the first and second opposing open ends, the first and the second opposing open ends of the open-ended recessed portion each at least in part defining respective portions of the outer periphery, the open-ended recessed portion being inset relative to the at least one outer surface of the distal end, the open-ended recessed portion extending along a single axis parallel with both the first and the second opposed recess surfaces such that the first and the second opposing open ends of the at least one open-ended recessed portion are positioned on the single axis, both the first and the second opposed recess surfaces extending away from a base of the open-ended recessed portion in a direction parallel to a longitudinal axis of the insertion tube; and at least two working channels enabling the operation of at least a surgical tool;

at least one basis guide positioned substantially within the at least one open-ended recessed portion of the distal end such that: (1) first and second opposing and spaced apart surfaces of the at least one basis guide are flush respectively with the first and second recess surfaces of the at least one open-ended recessed portion, (2) third and fourth opposing and spaced apart surfaces of the at least one basis guide are both flush relative to and positioned adjacent respective portions of the at least one outer surface of the distal end, and (3) the third and fourth surfaces of the at least one basis guide each have a curvature that is congruent to a curvature of the respective portions of the at least one outer surface of the distal end of the insertion tube; and at least two command means operatively associated with each of the at least two working channels, at least one of the at least two command means being configured to manipulate the at least one basis guide in one of a horizontal or a vertical direction independent of any movement of the distal end and of the insertion tube.

2. The endoscope according to claim 1, further comprising, in the distal end of the insertion tube at least one of an objective, an air/water channel, or a passage of light.

3. The endoscope according to claim 1, wherein one working channel has a smaller diameter and one working channel has a larger diameter.

4. The endoscope according to claim 3, wherein the at least one basis guide comprises a vertical basis guide operatively associated with the working channel of smaller diameter in the distal end of the insertion tube.

5. The endoscope according to claim 3, wherein the at least one basis guide comprises a horizontal basis guide operatively associated with the working channel of larger diameter in the distal end of the insertion tube.

6. The endoscope according to claim 4, wherein the vertical basis guide is commanded by a lever arranged on a knob and is fastened to the command means on its back portion.

7. The endoscope according to claim 5, wherein the horizontal basis guide is commanded by a rocker arm arranged on an operation section and is fastened to the command means on its back portion.

8. An endpiece defining a distal end of an insertion tube for an endoscope configured to perform surgeries through translumenal orifices in internal organs, said endpiece comprising: an outer periphery; at least one outer surface; at least one open-ended recessed portion having first and second opposing open ends and first and second opposing and spaced apart surfaces each extending continuously between the first and second opposing open ends, the first and the second opposing open ends of the open-ended recessed portion each intersecting and at least in part defining respective portions of the outer periphery, the open-ended recessed portion being inset relative to the at least one outer surface of the endpiece, the open-ended recessed portion extending along a single axis parallel with both the first and the second opposing and spaced apart surfaces such that the first and the second opposing open ends of the at least one open-ended recessed portion are positioned on a common axis, the common axis being the single axis, both the first and the second opposing and spaced apart surfaces extending away from a base of the open-ended recessed portion in a direction parallel to a longitudinal axis of the insertion tube; at least two working channels; at least one basis guide positioned substantially within the at least one open-ended recessed portion of the endpiece such that: (1) first and second opposing and spaced apart surfaces of the at least one basis guide are flush respectively with the first and second opposing and spaced apart surfaces of the at least one open-ended recessed portion, (2) third and fourth opposing and spaced apart surfaces of the at least one basis guide are both flush relative to and positioned adjacent respective portions of the at least one outer surface of the distal end, and (3) the third and fourth surfaces of the at least one basis guide each at least in part define respective portions of the outer periphery of the endpiece for the distal end of the insertion tube; and at least two command means operatively associated with each of the at least two working channels, at least one of the at least two command means being configured to manipulate the at least one basis guide in one of a horizontal or a vertical direction independent of any movement of the distal end and of the insertion tube.

9. A distal end portion of an insertion tube for an endoscope configured to perform surgeries through translumenal orifices in internal organs, said distal end portion comprising: an outer periphery; at least one outer surface; at least one open-ended recessed portion having first and second opposing open ends and first and second opposing and spaced apart surfaces each extending continuously between the first and second opposing open ends, the first and the second opposing open ends of the open-ended recessed portion each intersecting and at least in part defining respective portions of the outer periphery, the open-ended recessed portion being inset relative to the at least one outer surface of the distal end, the open-ended recessed portion extending along a single axis parallel with both the first and the second opposing and spaced apart surfaces such that the first and the second opposing open ends of the at least one open-ended recessed portion are positioned on a common axis, the common axis being the single axis, both the first and the second spaced apart surfaces extending away from a base of the open-ended recessed portion in a direction parallel to a longitudinal axis of the distal end portion of the insertion tube: at least two working channels, the working channels enabling the operation of a surgical tool; at least one basis guide positioned substantially within the at least one open-ended recessed portion of the distal end such that: (1) first and second opposing and spaced apart surfaces of the at least one basis guide are flush respectively with the first and second opposing and spaced apart surfaces of the at least one open-ended recessed portion, (2) third and fourth opposing and spaced apart surfaces of the at least one basis guide are both flush relative to and positioned adjacent respective portions of the at least one outer surface of the distal end, and (3) the third and fourth surfaces of the at least one basis guide each at least in part define respective portions of the outer periphery of the distal end of the insertion tube; and at least two command means operatively associated with each of the at least two working channels, at least one of the at least two command means being configured to manipulate the at least one basis guide in one of a horizontal or a vertical direction independent of any movement of the distal end and of the insertion tube.

10. Endoscope to perform surgeries through translumenal orifices in internal organs, said endoscope comprising: an insertion tube comprising: a distal end having an outer periphery, at least one outer surface, and a first open-ended recessed portion having first and second opposing open ends, and a second open-ended recessed portion having one open end and one closed end, the one closed end of the second open-ended recessed portion being defined by at least one surface of the first open-ended recessed portion, the at least one surface being intermediate the first and second opposing open ends of the first open-ended recessed portion, the first and the second opposing open ends of the first open-ended recessed portion each intersecting and at least in part defining respective portions of the outer periphery, the first open-ended recessed portion being inset relative to the at least one outer surface of the distal end, the first open-ended recessed portion extending along a first single axis such that the first and the second opposing open ends thereof are positioned on the first single axis, the second open-ended recessed portion extending along a second single axis, the second single axis being perpendicular to the first single axis; and at least two working channels enabling the operation of at least a surgical tool; at least one basis guide positioned substantially within the first open-ended recessed portion of the distal end such that a portion of the at least one basis guide is flush relative to and positioned adjacent a portion of the at least one outer surface of the distal end and such that the portion of the at least one basis guide has a curvature that is congruent to a curvature of the portion of the at least one outer surface of the distal end of the insertion tube; and at least two command means operatively associated with each of the at least two working channels, at least one of the at least two command means being configured to manipulate the at least one basis guide in one of a horizontal or a vertical direction independent of any movement of the distal end and of the insertion tube.

11. The endoscope of claim 10, wherein both the first and the second single axes are further perpendicular to a longitudinal axis of the insertion tube.

* * * * *